(12) United States Patent
Delorme et al.

(10) Patent No.: US 7,494,495 B2
(45) Date of Patent: Feb. 24, 2009

(54) METHOD AND IMPLANT FOR CURING CYSTOCELE

(75) Inventors: Emmanuel Delorme, Chalon sur Saone (FR); Georges Eglin, Beziers (FR); Jean-Marc Beraud, Saint-Etienne (FR)

(73) Assignee: Coloplast A/S, Humlebaek (DK)

( * ) Notice: Subject to any disclaimer, the term of this patent is extended or adjusted under 35 U.S.C. 154(b) by 448 days.

(21) Appl. No.: 10/809,798

(22) Filed: Mar. 26, 2004

(65) Prior Publication Data

US 2004/0249397 A1    Dec. 9, 2004

(30) Foreign Application Priority Data

Mar. 28, 2003   (FR) .................................. 03 03895

(51) Int. Cl.
*A61B 17/08* (2006.01)
*A61F 2/00* (2006.01)

(52) U.S. Cl. ......................................... 606/151; 600/37

(58) Field of Classification Search ................ 606/151, 606/193; 600/29, 30, 37
See application file for complete search history.

(56) References Cited

U.S. PATENT DOCUMENTS

| | | | |
|---|---|---|---|
| 2,199,690 A * | 5/1940 | Bullard ................... | 128/207.11 |
| 2,738,790 A | 3/1956 | Todt, Sr. et al. | |
| 3,124,136 A | 3/1964 | Usher | |
| 3,182,662 A | 5/1965 | Shirodkar | |
| 3,311,110 A | 3/1967 | Singerman et al. | |
| 3,384,073 A | 5/1968 | Van Winkle, Jr. | |
| 3,472,232 A | 10/1969 | Earl | |
| 3,580,313 A | 5/1971 | McKnight | |
| 3,763,860 A | 10/1973 | Clarke | |
| 3,789,828 A | 2/1974 | Schulte | |
| 3,858,783 A | 1/1975 | Kapitanov et al. | |
| 3,924,633 A | 12/1975 | Cook et al. | |
| 3,995,619 A | 12/1976 | Glatzer | |
| 4,019,499 A | 4/1977 | Fitzgerald | |
| 4,037,603 A | 7/1977 | Wendorff | |

(Continued)

FOREIGN PATENT DOCUMENTS

DE          2 305 815          8/1974

(Continued)

OTHER PUBLICATIONS

Aldridge, "Transplantation of Fascia for Relief for Relief of Urinary Stress Incontinence," *Am. J. Obstet. Gynecol.*, 1942, 44:398-411.

(Continued)

*Primary Examiner*—Julian W Woo
*Assistant Examiner*—Dianne Dornbusch
(74) *Attorney, Agent, or Firm*—Fish & Richardson, P.C.; Walter K. Roloff (57) ABSTRACT

The invention concerns an implant for the treatment of cystocele, having a thin and supple structure, characterized in that it comprises a support body (2) from which extend at least: two anterior suspension straps (3) arranged on both sides of the sagittal plane (S), two posterior suspension straps (4), arranged on both sides of the sagittal plane (S), and two middle suspension straps (5) arranged on both sides of the sagittal plane (S) and between the anterior and posterior straps (3) and (4). Application to the treatment of cystocele.

34 Claims, 3 Drawing Sheets

U.S. PATENT DOCUMENTS

| | | | |
|---|---|---|---|
| 4,128,100 | A | 12/1978 | Wendorff |
| 4,172,458 | A | 10/1979 | Pereyra |
| 4,235,238 | A | 11/1980 | Ogui et al. |
| 4,246,660 | A | 1/1981 | Wevers |
| 4,441,497 | A | 4/1984 | Paudler |
| 4,509,516 | A | 4/1985 | Richmond |
| 4,632,100 | A | 12/1986 | Somers et al. |
| 4,775,380 | A | 10/1988 | Seedhom et al. |
| 4,857,041 | A | 8/1989 | Annis et al. |
| 4,865,031 | A | 9/1989 | O'Keeffe |
| 4,920,986 | A | 5/1990 | Biswas |
| 5,013,292 | A | 5/1991 | Lemay |
| 5,053,043 | A | 10/1991 | Gottesman et al. |
| 5,085,661 | A | 2/1992 | Moss |
| 5,112,344 | A | 5/1992 | Petros |
| 5,123,428 | A | 6/1992 | Schwarz |
| 5,188,636 | A | 2/1993 | Fedotov |
| 5,207,694 | A | 5/1993 | Broomé |
| 5,209,756 | A | 5/1993 | Seedhom et al. |
| 5,250,033 | A | 10/1993 | Evans et al. |
| 5,256,133 | A | 10/1993 | Spitz |
| 5,281,237 | A | 1/1994 | Gimpelson |
| 5,328,077 | A | 7/1994 | Lou |
| 5,336,239 | A | 8/1994 | Gimpelson |
| 5,337,736 | A | 8/1994 | Reddy |
| 5,362,294 | A | 11/1994 | Seitzinger |
| 5,368,595 | A | 11/1994 | Lewis |
| 5,383,904 | A | 1/1995 | Totakura et al. |
| 5,386,836 | A | 2/1995 | Biswas |
| 5,403,328 | A | 4/1995 | Shallman |
| 5,413,598 | A | 5/1995 | Moreland |
| 5,439,467 | A | 8/1995 | Benderev et al. |
| 5,507,796 | A | 4/1996 | Hasson |
| 5,520,700 | A | 5/1996 | Beyar et al. |
| 5,544,664 | A | 8/1996 | Benderev et al. |
| 5,562,685 | A | 10/1996 | Mollenauer et al. |
| 5,562,689 | A | 10/1996 | Green et al. |
| 5,571,139 | A | 11/1996 | Jenkins, Jr. et al. |
| 5,591,163 | A | 1/1997 | Thompson |
| 5,611,515 | A | 3/1997 | Benderev et al. |
| 5,628,756 | A | 5/1997 | Barker, Jr. et al. |
| 5,633,286 | A | 5/1997 | Chen |
| 5,669,935 | A | 9/1997 | Rosenman et al. |
| 5,683,349 | A | 11/1997 | Makower et al. |
| 5,807,403 | A | 9/1998 | Beyar et al. |
| 5,836,314 | A | 11/1998 | Benderev et al. |
| 5,836,315 | A | 11/1998 | Benderev et al. |
| 5,842,478 | A | 12/1998 | Benderev et al. |
| 5,860,425 | A | 1/1999 | Benderev et al. |
| 5,899,909 | A | 5/1999 | Claren et al. |
| 5,919,232 | A | 7/1999 | Chaffringeon et al. |
| 5,934,283 | A | 8/1999 | Willem et al. |
| 5,935,122 | A | 8/1999 | Fourkas et al. |
| 5,944,732 | A | 8/1999 | Raulerson et al. |
| 5,972,000 | A | 10/1999 | Beyar et al. |
| 5,988,171 | A | 11/1999 | Sohn et al. |
| 5,997,554 | A | 12/1999 | Thompson |
| 6,010,447 | A | 1/2000 | Kardjian |
| 6,030,393 | A | 2/2000 | Corlew |
| 6,031,148 | A | 2/2000 | Hayes et al. |
| 6,039,686 | A | 3/2000 | Kovac |
| 6,042,534 | A | 3/2000 | Gellman et al. |
| 6,042,536 | A | 3/2000 | Tihon et al. |
| 6,048,351 | A | 4/2000 | Gordon et al. |
| 6,050,937 | A | 4/2000 | Benderev |
| 6,053,935 | A | 4/2000 | Brenneman et al. |
| 6,068,591 | A | 5/2000 | Bruckner et al. |
| 6,071,290 | A | 6/2000 | Compton |
| 6,074,341 | A | 6/2000 | Anderson et al. |
| 6,106,545 | A | 8/2000 | Egan |
| 6,110,101 | A | 8/2000 | Tihon et al. |
| 6,113,623 | A * | 9/2000 | Sgro .................... 606/215 |
| 6,117,067 | A | 9/2000 | Gil-Vernet |
| 6,168,611 | B1 | 1/2001 | Rizvi |
| 6,221,005 | B1 | 4/2001 | Bruckner et al. |
| 6,273,852 | B1 | 8/2001 | Lehe et al. |
| 6,302,840 | B1 | 10/2001 | Benderev |
| 6,306,079 | B1 | 10/2001 | Trabucco |
| 6,328,744 | B1 | 12/2001 | Harari et al. |
| 6,334,446 | B1 | 1/2002 | Beyar |
| 6,352,553 | B1 | 3/2002 | van der Burg et al. |
| 6,382,214 | B1 | 5/2002 | Raz et al. |
| 6,406,423 | B1 | 6/2002 | Scetbon |
| 6,406,480 | B1 | 6/2002 | Beyar et al. |
| 6,475,139 | B1 | 11/2002 | Miller |
| 6,478,727 | B2 | 11/2002 | Scetbon |
| 6,482,214 | B1 | 11/2002 | Sidor, Jr. et al. |
| 6,494,887 | B1 | 12/2002 | Kaladelfos |
| 6,494,906 | B1 | 12/2002 | Owens |
| 6,502,578 | B2 | 1/2003 | Raz et al. |
| 6,530,943 | B1 | 3/2003 | Hoepffner et al. |
| 6,575,897 | B1 | 6/2003 | Ory et al. |
| 6,582,443 | B2 | 6/2003 | Cabak et al. |
| 6,612,977 | B2 | 9/2003 | Staskin et al. |
| 6,638,211 | B2 | 10/2003 | Suslian et al. |
| 6,776,161 | B2 * | 8/2004 | Horn .................... 128/207.11 |
| 6,786,861 | B1 | 9/2004 | Pretorius |
| 2001/0000533 | A1 | 4/2001 | Kovac |
| 2001/0018549 | A1 | 8/2001 | Scetbon |
| 2001/0039423 | A1 | 11/2001 | Skiba et al. |
| 2001/0049467 | A1 | 12/2001 | Lehe et al. |
| 2002/0007222 | A1 | 1/2002 | Desai |
| 2002/0022841 | A1 | 2/2002 | Kovac |
| 2002/0028980 | A1 | 3/2002 | Thierfelder et al. |
| 2002/0055748 | A1 | 5/2002 | Gellman et al. |
| 2002/0058959 | A1 | 5/2002 | Gellman |
| 2002/0068948 | A1 | 6/2002 | Stormby et al. |
| 2002/0072694 | A1 | 6/2002 | Snitkin et al. |
| 2002/0077526 | A1 | 6/2002 | Kammerer et al. |
| 2002/0078964 | A1 | 6/2002 | Kovac et al. |
| 2002/0082619 | A1 | 6/2002 | Cabak et al. |
| 2002/0083949 | A1 | 7/2002 | James |
| 2002/0091298 | A1 | 7/2002 | Landgrebe |
| 2002/0091373 | A1 | 7/2002 | Berger |
| 2002/0099258 | A1 | 7/2002 | Staskin et al. |
| 2002/0099259 | A1 | 7/2002 | Anderson et al. |
| 2002/0099260 | A1 | 7/2002 | Suslian et al. |
| 2002/0103542 | A1 | 8/2002 | Bilbo |
| 2002/0107430 | A1 | 8/2002 | Neisz et al. |
| 2002/0107525 | A1 | 8/2002 | Harari et al. |
| 2002/0115906 | A1 | 8/2002 | Miller |
| 2002/0119177 | A1 | 8/2002 | Bowman et al. |
| 2002/0128670 | A1 | 9/2002 | Ulmsten et al. |
| 2002/0138025 | A1 | 9/2002 | Gellman et al. |
| 2002/0147382 | A1 | 10/2002 | Neisz et al. |
| 2002/0151762 | A1 | 10/2002 | Rocheleau et al. |
| 2002/0151909 | A1 | 10/2002 | Gellman et al. |
| 2002/0151910 | A1 | 10/2002 | Gellman et al. |
| 2002/0156487 | A1 | 10/2002 | Gellman et al. |
| 2002/0156488 | A1 | 10/2002 | Gellman et al. |
| 2002/0183588 | A1 | 12/2002 | Fierro |
| 2002/0188169 | A1 | 12/2002 | Kammerer et al. |
| 2003/0004395 | A1 | 1/2003 | Therin |
| 2003/0009181 | A1 | 1/2003 | Gellman et al. |
| 2003/0023136 | A1 | 1/2003 | Raz et al. |
| 2003/0023137 | A1 | 1/2003 | Gellman |
| 2003/0023138 | A1 | 1/2003 | Luscombe |
| 2003/0036676 | A1 | 2/2003 | Scetbon |
| 2003/0050530 | A1 | 3/2003 | Neisz et al. |
| 2003/0065246 | A1 | 4/2003 | Inman et al. |
| 2003/0065402 | A1 | 4/2003 | Anderson et al. |
| 2003/0078468 | A1 | 4/2003 | Skiba et al. |
| 2003/0100954 | A1 | 5/2003 | Schuldt-Hempe et al. |
| 2003/0130670 | A1 | 7/2003 | Anderson et al. |

| | | | |
|---|---|---|---|
| 2003/0149440 A1 | 8/2003 | Kammerer et al. | |
| 2003/0171644 A1 | 9/2003 | Anderson et al. | |
| 2003/0176762 A1 | 9/2003 | Kammerer | |
| 2003/0176875 A1 | 9/2003 | Anderson et al. | |
| 2003/0212305 A1 | 11/2003 | Anderson et al. | |
| 2003/0220538 A1* | 11/2003 | Jacquetin | 600/37 |
| 2004/0039453 A1 | 2/2004 | Anderson et al. | |
| 2004/0097974 A1 | 5/2004 | DeLaval | |
| 2004/0116774 A1* | 6/2004 | Migliari | 600/37 |
| 2004/0231678 A1 | 11/2004 | Fierro | |
| 2004/0243166 A1 | 12/2004 | Odermatt et al. | |
| 2004/0249240 A1 | 12/2004 | Goldmann et al. | |
| 2005/0080317 A1 | 4/2005 | Merade | |
| 2005/0107805 A1 | 5/2005 | Bouffier et al. | |
| 2005/0240076 A1 | 10/2005 | Niesz et al. | |
| 2005/0278037 A1 | 12/2005 | Delorme et al. | |
| 2006/0173237 A1* | 8/2006 | Jacquetin | 600/29 |

FOREIGN PATENT DOCUMENTS

| | | |
|---|---|---|
| DE | 4 220 283 | 12/1993 |
| DE | 4 304 353 | 4/1994 |
| EP | 0 470 308 | 2/1992 |
| EP | 0 643 945 | 3/1995 |
| EP | 1 093 758 | 4/2001 |
| EP | 0 774 240 | 3/2003 |
| EP | 0 650 703 | 5/2005 |
| FR | 2785521 | 5/1997 |
| FR | 2 785 521 | 5/2000 |
| GB | 378288 A | 8/1932 |
| RU | 2187251 C1 | 8/2002 |
| RU | 2196518 C2 | 1/2003 |
| SU | 1 225 547 | 4/1986 |
| SU | 1 342 486 | 10/1987 |
| SU | 1475607 A1 | 4/1989 |
| WO | WO 93/17635 | 9/1993 |
| WO | WO 93/19678 | 10/1993 |
| WO | WO 98/19606 | 5/1998 |
| WO | WO 98/35606 | 8/1998 |
| WO | WO 98/35616 | 8/1998 |
| WO | WO 98/35632 | 8/1998 |
| WO | WO 99/52450 | 10/1999 |
| WO | WO 00/09039 | 2/2000 |
| WO | WO 00/13601 | 3/2000 |
| WO | WO 00/18319 | 4/2000 |
| WO | WO 00/57812 | 10/2000 |
| WO | WO 00/64370 | 11/2000 |
| WO | WO 00/74594 | 12/2000 |
| WO | WO 00/74613 | 12/2000 |
| WO | WO 00/74633 | 12/2000 |
| WO | WO 01/06951 | 2/2001 |
| WO | WO-0106951 A1 | 2/2001 |
| WO | WO 01/26581 | 4/2001 |
| WO | WO 01/39670 | 6/2001 |
| WO | WO 01/45589 | 6/2001 |
| WO | WO-0152729 A2 | 7/2001 |
| WO | WO 01/56499 | 8/2001 |
| WO | WO 02/02031 | 1/2002 |
| WO | WO 02/26108 | 4/2002 |
| WO | WO 02/28312 | 4/2002 |
| WO | WO 02/32284 | 4/2002 |
| WO | WO-0232346 A1 | 4/2002 |
| WO | WO 02/34124 | 5/2002 |
| WO | WO 02/38079 | 5/2002 |
| WO | WO 02/39890 | 5/2002 |
| WO | WO-0239890 A2 | 5/2002 |
| WO | 02058563 | 8/2002 |
| WO | WO 02/058563 | 8/2002 |
| WO | WO-02065921 A1 | 8/2002 |
| WO | WO 02/069781 | 9/2002 |
| WO | WO 02/071953 | 9/2002 |
| WO | WO 02/078552 | 10/2002 |
| WO | WO 03/068107 | 8/2003 |
| WO | WO 03/073960 | 9/2003 |
| WO | WO 03/096929 | 11/2003 |
| WO | WO2004/012626 | 2/2004 |

OTHER PUBLICATIONS

Araki et al., "The Loop-Loosening Procedure for Urination Difficulties After Stamey Suspension of the Vesical Neck," *J. Urol.*, 1990, 144:319-323.

Asmussen and Ulmsten, "Simultaneous Urethro-Cystometry with a New Technique," *Scand. J. Urol. Nephrol.*, 1976, 10:7-11.

Beck and McCormick, "Treatment of Urinary Stress Incontinence with Anterior Colporrhaphy," *Obstetrics and Gynecology*, 1982, 59(3):271-274.

Benderev, "Anchor Fixation and Other Modification of Endoscopic Bladder Neck Suspension," *Urology*, 1992, 40(5): 409-418.

Benderev, "A Modification Percutaneous Outpatient Bladder Neck Suspension System," *J. Urol.*, 1994, 152:2316-2320.

Bergman and Elia, "Three surgical procedures for genuine stress incontinence: Five-year follow-up of a prospective randomized study," *Am. J. Obstet. Gynecol.*, 1995, 173:66-71.

Blaivas and Jacobs, "Pubovaginal Fascial Sling for the Treatment of Complicated Stress Urinary Incontinence," *J. Urol.*, 145:1214-1218.

Blaivas and Salinas, "Type III Stress Urinary Incontinence: Importance of Proper Diagnosis and Treatment, " *American College of Surgeons Surgical Forum*, 1984, 70th Annual Clinical Congress, San Francisco, CA, vol. XXXV, pp. 473-474.

Bryans, "Marlex gauze hammock sling operation with Cooper's ligament attachment in the management of recurrent urination stress incontinence," *Am. J. Obstet. Gynecol.*, 1979, 133(3):292-294.

Burch, "Urethrovaginal fixation to Cooper's ligament for correction of stress incontinence, cystocele, and prolapse," *Am. J. Obstet. Gynecol.*, 1961, 81(2):281-290.

Choe and Staskin, "Gore-Tex Patch Sling: 7 Years Later," *Urology.*, 1999, 54:641-646.

Chopra et al., "Technique of Rectangular Fascial Sling," *Female Urology*, 1996, Raz (ed.), W.B. Saunders Company, Chapter 34, pp. 392-394.

Daregent et al., "Insertion of a sub urethral sling through the obturating membrane in the treatment of female urinary incontinence," *Gynécol. Obstér. Fértil.*, 2002, 30:576-582.

Das and Palmer, "Laparoscopic Colpo-Suspension," *J. Urol.*, 1995, 154:1119-1121.

Decter, "Use of the Fascial Sling for Neurogenic Incontinence: Lessons Learned," *J. Urol.*, 1993, 150:683-686.

Delorme, "The transobturator tape: A minimally invasive procedure for treating female stress urinary incontinence," *Progrés en Urologie.*, 2001, 11:1306-1313 (w/English translation).

Eglin et al., "Transobturator subvesical mesh. Tolerance and short-term results of a 103 case continous series," *Gynécologie Obstétrique & Fertilité.*, 2003, 31:14-19 (English translation including).

Enzelsberger et al., "Urodynamic and Radiologic Parameters Before and After Loop Surgery for Recurrent Urinary Stress Incontinence," *Acta Obstet. Gynecol. Scand.*, 1990, 69:51-54.

Eriksen et al., "Long-Term Effectiveness of the Burch Colposuspension Female Urinary Stress Incontinence," *Acta Obstet. Gynecol. Scand.*, 1990, 69:45-50.

Falconer et al., "Clinical Outcome and Changes in Connective Tissue Metabolism After Intravaginal Slingplasty in Stress Incontinence Women," *Int. Urogynecol. J.*, 1996, 7:133-137.

Falconer et al., "Influence of Different Sling Materials on Connective Tissue Metabolism in Stress Urinary Incontinence Women," *Int. Urogynecol. J.*, 2001, (Suppl. 2):S19-S23.

Forum du Comité d'Urologie et de Périnéologie de la Femme, Le Trou Obturé: Limites et Dangers (V. Delmas), URL: http://www.ruofrance.org/congress.php?op=2003_11_22_01, (English translation included), printed from the internet on May 12, 2006, 5 pages.

Gilja et al., "A Modified Raz Bladder Neck Suspension Operation (Transvaginal Burch)," *J. Urol.*, 1995, 153:1455-1457.

Gittes and Loughlin, "No-Inclusion Pubovaginal Suspension for Stress Incontinence," *J. Urol.*, 1987, 138:568-570.

Gruss, "The Obturator Bypass. Indications. Techniques. Outcomes," *Chirurgie.*, 1971, 97:220-226 (w/English translation).

Guida and Moore, "The Surgeon At Work. Obturator Bypass Technique," *Surgery, Gynecology & Obstetrics*, 1969, pp. 1307-1315.

Handa et al., "Banked Human Fascia Lata for the Suburethral Sling Procedure: A Preliminary Report," *Obstet. Gynecol.*, 1996, 88:1045-1049.

Henriksson and Ulmsten, "A urodynamic evaluation of the effects of abdominal urethrocystopexy and vaginal sling urethroplasty in women with stress incontinence," *Am. J. Obstet. Gynecol.*, 1978, 131:77-82.

Hodgkinson and Kelly, "Urinary Stress Incontinence in the Female. III. Round-ligament technique for retropubic suspension of the urethra," *Obstet. Gynecol.*, 1957, 10:493-499.

Hohenfellner and Petri, "Sling Procedures," *Surgery of Female Incontinence*, 2nd edition, Springer-Verlag, pp. 105-113.

Holschneider et al., "The Modified Pereyra Procedure in Recurrent Stress Urinary Incontinence: A 15-Year Review," *Obstet. Gynecol.*, 1994, 83:573-578.

Horbach et al., "A Suburethral Sling Procedure with Polytetrafluoroethylene for the Treatment of Genuine Stress Incontinence in Patients with Low Urethral Closure Pressure," *Obstet. Gynecol.*, 1988, 71:648-652.

Horbach, "Suburethral Sling Procedures," *Urogynecology and Urodynamics-Theory and Practice*, 1996, Williams & Wilkins, pp. 596-579.

Ingelman-Sundberg and Ulmsten, "Surgical Treatment of Female Urinary Stress Incontinence," *Contr. Gynec. Obstet.*, 1983, 10:51-69.

Jeffcoate, "The Results of the Aldridge Sling Operation for Stress Incontinence," *The Journal of Obstetrics and Gynaecology of the British Empire*, 1956, 63:36-39.

Jeter, "The Social Impact of urinary Incontinence," *Female Urology*, 1983, 2nd edition, Raz (ed.), Chapter 7, pp. 80-86.

Karram and Bhatia, "Patch Procedure: Modified Transvaginal Fascia Lata Sling For Recurrent or Severe Stress Urinary Incontinence," *Obstet. Gynecol.*, 1990, 75:461-463.

Kerdiles et al., "Bypass via the Obturator Foramen in Reconstructive Arterial Surgery of the Lower Extremities," *Ann. Chir. Thorac. Cardio-Vasc.*, 1974, 13(4):335-341 (w/English translation).

Kerr and Staskin, "The Use of Artificial Material for Sling Surgery in the Treatment of Female Stress Urinary Incontinence," *Female Urology*, 1996, Raz (ed.), W.B. Saunders Company, Chapter 33, pp. 382-391.

Kersey, "The gauze hammock sling operation in the treatment of stress incontinence," *Br. J. Obstet. Gynecol.*, 1983, 90:945-949.

Klutke et al., "The Anatomy of Stress Incontinence: Magnetic Resonance Imaging of the Female Bladder Neck and Uretha," *J. Urol.*, 1990, 143:563-566.

Klutke et al., "Transvaginal Bladder Neck Suspension to Cooper's Ligament: A Modified Pereyra Procedure," *Obstet. Gynecol.*, 1996, 88:294-297.

Korda et al., "Experience with Silastic Slings for Female Urinary Incontinece," *Aust. NZ J. Obstet Gynaecol.*, 1989, 29:150-154.

Kovac, "Follow-up of the Pubic Bone Suburethral Stabilization Sling Operation for Recurrent Urinary Incontinence (Kovac Procedure)," *J. Pelvic Surgery*, 1999, 5(3):156-160.

Kovac and Cruikshank, "Pubic Suburethral Stabilization Sling for Recurrent Urinary Incontinence," *Obstet. Gynecol.*, 1997, 98:624-627.

Kovac and Cruikshank, "Pubic bone suburethral stabilization sling: a long-term cure for SUI?" *Contemporary OB/GYN*, 1998, 43(2):51-72.

Leach, "Bone Fixation Technique for Transvaginal Needle Suspension," *Urology*, 1988, 31(5):388-390.

Leach et al., "Female Stress Urinary Incontinence Clinical Guidelines Panel Summary Report on Surgical Management of Female Stress Urinary Incontinence," *J. Urol.*, 1997, 158:875-880.

Leval, "Noval Surgical Technique for the Treatment of Female Stress Urinary Continence: Transobturator Vaginal Tape Inside-Out," *European Urology*, 2003, 44: 724-730.

Lichtenstein et al., "The Tension-Free Hernioplasty," *Am. J. Surgery.*, 1989, 157:188-193.

Loughlin et al., "Review of an 8-Year Experience with Modifcations of Endoscopic Suspension of the Bladder Neck for Female Stress Urinary Incontinence," *J. Urol.*, 1990, 143:44-45.

Mahoney and Whelan, "Use of Obturator Foramen in Iliofemoral Artery Grafting: Case Reports," *Annals of Surgery*, 1966, 163(2):215-220.

McGuire, "Abdominal Procedures for Stress Incontinence," *Urologic Clinics of North America*, 1985, 12(2):285-290.

McGuire et al., "Experience with Pubovaginal Slings for Urinary Incotinence at the University of Michigan," *J. Urol.*, 1987, 138:525-526.

McGuire and Lytton, "Pubovaginal Sling Procedure for Stress Incontinence," *J. Urol.*, 1978, 119:82-84.

McIndoe et al., "The Aldridge Sling Procedure in the Treatment of Urinary Stress Incontinence," *Aust. NZ J. Obstet. Gynaecol.*, 1987, 27:238:239.

McKiel, Jr. et al., "Marshall-Marchetti Procedure: Modification," *J. Urol.*, 1966, 96:737-739.

Marshall et al., "The Correction of Stress Incontinence by Simple Vesicourethral Suspension," *J. Urol.*, 2002, 168:1326-1331.

McGuire and Gormley, "Abdominal Fascial Slings," *Female Urology*, 1996, Raz (ed.), W.B. Saunders Company, Chapter 31, pp. 369-375.

Moir, "The Gauze-Hammock Operation," *The Journal of Obstetrics and Gynaecology of the British Commonwealth*, 1968, 75(1):1-9.

Morgan et al., "The Marlex sling operation for the treatment of recurrent stress urinary incontinence: A 16-year review," *Am. J. Obstet. Gynecol.*, 1985, 151:224-226.

Morgan, "A sling operation, using Marlex polypropylene mesh, for treatment of recurrent stress incontinence," *Am. J. Obstet. Gynecol.*, 1970, 106(3):369-376.

Narik and Palmrich, "A simplified sling operation suitable for use," *Am. J. Obstet. Gynecol.*, 1962, 84:400-405.

Nichols, "The Mersilene Mesh Gauze-Hammock For Severe Urinary Stress Incontinence," *Obstet. Gynecol.*, 1973, 41(1):88-93.

Nickel et al., "Evaluation of a Transpelvic Sling Procedure With and Without Colpolsuspension for Treatment of Female Dogs With Refractory Urethral Sphincter Mechanism Incompetence," *Veterinary Surgery*, 1998, 27:94-104.

Norris et al., "Use of Synthetic Material in Sling Surgery: A Minimally Invasive Approach," *J. Endocrinology*, 1996, 10(3):227-230.

Novak, "Abdonomovaginal techniques," *Gynecological Surgical Technique*, Piccin Editore, Padua, 5 pages (English translation included).

O'Donnell, "Combined Raz Urethral Suspension and McGuire Pubovaginal Sling for Treatment of Complicated Stress Urinary Incontinence," *J. Arkansas Medical Society*, 1992, 88(8):389.

Parra and Shaker, "Experience with a Simplified Technique for the Treatment of Female Stress Urinary Incontinence," *British Journal of Urology*, 1990, 66:615-617.

Pelosi III and Pelosi, "Pubic Bone Suburethral Stabilization Sling: Laparoscopic Assessment of a Transvaginal Operation for the Treatment of Stress Urinary Incontinence," *Journal of Laparoendoscopic & Advanced Surgical Techniques*, 1999, 9(1):45-50.

Pelosi II and Pelosi III, "New transobturator sling reduces risk of injury," *OBG Management*, 2003, pp. 17-37.

Penson and Raz, "Why Anti-Incontinence Surgery Succeeds or Fails," *Female Urology*, 1996, Raz (ed.), W.B. Saunders Company, Chapter 41, pp. 435-442.

Pereyra et al., "Pubourethral Supports in Perspective: Modified Pereyra Procedure for Urinary Incontinence," *Obstet. Gynecol.*, 1982, 59:643-648.

Petros and Ulmsten, "An analysis of rapid pad testing and the history for the diagnosis of stress incontinence," *Acta Obstet. Gynecol. Scand.*, 1992, 71:529-536.

Petros and Ulmsten, "An Anatomical Basis for Success and Failure of Female Incontinence Surgery," *Scand. J. Urol. Nephrol.*, 1993, (Suppl. 3):55-60.

Petros and Konsky, "Anchoring the midurethral rrestores bladder-neck anatomy and continence," *The Lancet*, 1999, 354:997-998.

Petros et al., "The Autogenic Ligament Procedure: A Technique for Planned Formation of an Artificial Neo-Ligament," *Acta Obstet. Gynecol. Scand.*, 1990, 69(Suppl. 153):43-51.

Petros and Ulmsten, "Bladder Instability in Women: A Premature Activation of the Micturition Reflex," *Neurourology and Urodynamics.*, 1993, 12:235-239.

Petros and Ulmsten, "The Combined Intravaginal Sling and Tuck Operation. An Ambulatory Procedure Cure of Stress and Urge Incontinence," *Acta Obstet. Gynecol. Scand.*, 1990, 69(Suppl. 153):53-59.

Petros and Ulmsten, "Cough Transmission Ratio: An Indicator of Suburethral Vaginal Wall Tension Rather than Urethral Closure?" *Acta Obstet. Gynecol. Scand.*, 1990, 69(Suppl. 153):37-38.

Petros and Ulmsten, "Cure of Stress Incontinence by Repair of External Anal Sphincter," *Acta Obstet. Gynecol. Scand.*, 1990, 69(Suppl. 153):75.

Petros and Ulmsten, "Cure of Urge Incontinence by the Combined Intravaginal Sling and Tuck Operation," *Acta Obstet. Gynecol. Scand.*, 1990, 69(Suppl. 153)61-62.

Petros, "Development of Generic Models for Ambulatory Vaginal Surgery—a Preliminary Report," *Int. Urogynecol. J.*, 1998, 9:19-27.

Petros and Ulmsten, "The Development of the Intravaginal Slingplasty Procedure: IVS II—(with bilateral "tucks ")," *Scand. J. Urol. Nephrol.*, 1993, Suppl. 153:61-67.

Petros and Ulmsten, "The Free Graft Procedure for Cure of the Tethered Vagina Syndrome," *Scand. J. Urol. Nephrol.*, 1993, Suppl. 153: 85-87.

Petros and Ulmsten, "Further Development of the Intravaginal Slingplasty Procedure—IVS III—(with midline "tuck ")," *Scand. J. Urol. Nephrol.*, 1993, Suppl. 153:69-71.

Petros and Ulmsten, "The Further Development of the Intravaginal Slingplasty Procedure: IVS IV—(with "double-breasted" unattached vaginal flap repair and "free " vaginal tapes)," *Scand. J. Urol. Nephrol.*, 1993, Suppl. 153:73-79.

Petros and Ulmsten, "An Integral Theory of Female Urinary Incontinence," *Acta Obstet. Gynecol. Scand.*, 1990, 69(Suppl. 153):7-31.

Petros and Ulmsten, "The Intravaginal Slingplasty Procedure: IVS IV—further development of the "double-breasted" vaginal repair—attached flap," *Scand. J. Urol. Nephrol.*, 1993, Suppl. 153:81-84.

Petros and Ulmsten, "Non Stress Non Urge Female Urinary Incontinence—Diagnosis and Cure: A Preliminary Report," *Acta Obstet. Gynecol. Scand.*, 1990, 69(Suppl. 153):69-70.

Petros and Ulmsten, "Part I: Theoretical, Morphological, Radiographical Correlations and Clinical Perspective," *Scand. J. Urol. Nephrol.*, 1993, Suppl. 153:5-28.

Petros and Ulmsten, "Part II:The Biomechanics of Vaginal Tissue and supporting Ligaments with Special Relevance to the Pathogenesis of Female Urinary Incontinence," *Scand. J. Urol. Nephrol.*, 1993, Suppl. 153:29-40.

Petros and Ulmsten, "Part III: Surgical Principles Deriving from the Theory," *Scand. J. Urol. Nephrol.*, 1993, Suppl. 153:41-52.

Petros and Ulmsten, "Part IV: Surgical Applications of the Theory—Development of the Intravaginal Sling Plasty (IVS) Procedure," *Scand. J. Urol. Nephrol.*, 1993, Suppl. 153:53-54.

Petros and Ulmsten, "Pinch Test for Diagnosis of Stress Urinary Incontinence," *Acta Obstet. Gynecol. Scand.*, 1990, 69(Suppl. 153):33-35.

Petros and Ulmsten, "The Posterior Fornix Syndrome: A Multiple Symptom Complex of Pelvin Pain and Abnormal Urinary Symptoms Deriving from Laxity in the Posterior Fornix of Vagina," *Scand. J. Urol. Nephrol.*, 1993, Suppl. 153:89-93.

Petros and Ulmsten, "Pregnancy Effects on the Intravaginal Sling Operation," *Acta Obstet. Gynecol. Scand.*, 1990, 69(Suppl.153):77-78.

Petros and Ulmsten, "The Role of a Lax Posterior Vaginal Fornix in the Causation of Stress and Urgency Symptoms: A Preliminary Report," *Acta Obstet. Gynecol. Scand.*, 1990, 69(Suppl. 153):71-73.

Petros and Ulmsten, "The Tethered Vagina Syndrome, Post Surgical Incontinence and I-Plasty Operation for Cure," *Acta Obstet. Gynecol. Scand.*, 1990, 69(Suppl.153):63-67.

Petros and Ulmsten, "The Tuck Procedure: A Simplified Vaginal Repair for Treatment of Female Urinary Incontinence," *Acta Obstet. Gynecol. Scand.*, 1990, 69(Suppl.153):41-42.

Petros and Ulmsten, "Urethral Pressure Increase on Effort Originates From Within the Urethra, and Continence From Musculovaginal Closure," *Neurourology and Urodynamics.*, 1995, 14:337-350.

Rackley, "Synthetic slings: Five steps for successful placement—Follow these steps to insert Transvaginal/Percutaneous slings using vaginal approach alone," Urology Times, 2000, 28:46-49.

Rackley et al., "Tension-free Vaginal Tape and Percutaneous Vaginal Tape Sling Procedures," *Techniques in Urology*, 2001, 7(2):90-100.

Raz, "Modified Bladder Neck Suspension for Female Stress Incontinence," *Urology*, 1981, 17(1):82-85.

Raz et al., "Urological Neurology and Urodynamics," *J. Urol.*, 1992, 148:845-850.

Richardson et al., "Delayed Reaction to the Decron Buttress Used in Urethropexy," *J. Reproductive Med.*, 1984, 29(9):689-692.

Ridley, "Appraisal of the Goebell-Frangenheim-Stoeckel sling procedure," *Am. J. Obstet. Gynecol.*, 1966, 95(5):714-721.

Sheiner et al., "An unusual complication of obturator foremen arterial bypass," *J. Cardiovasc. Surg.*, 1969, 10(4):324-328.

Sirls and Leach, "Use of Fascia Lata for Pubovaginal Sling," *Female Urology*, 1996, Raz (ed.). W.B. Saunders Company, Chapter 32, pp. 376-381.

Sloan and Barwin, "Stress Incontinence of Urine: A Retrospective Study of the Complications and Late Results of Simple Suprapubic Suburethral Fascial Slings," *J. Urol.*, 1973, 110:533-536.

Spencer er al., "A Comparison of Endoscopic Suspension of the Vesical Neck with Suprapubic Vesicourethropexy for Treatment of Stress Urinary Incontinence," *J. Urol.*, 1987, 137:411-415.

Sterney, "Endoscopic Suspension of the Vesical Neck for Urinary Incontinence in Females," *Annals of Surgery.*, 1980, 192(4):465-471.

Stanton, "Suprapubic Approaches for Stress Incontinence in Women," *J. Am. Geriatrics Soc.*, 1990, 38(3):348-351.

Staskin et al., "The Gore-tex sling procedure for female sphincteric incontinence: indications, technique, and results," *World J. Urol.*, 1997, 15:295-299.

Stothers et al., "Anterior Vaginal Wall Sling," *Female Urology*, 1996, Raz (ed.), W.B. Saunders Company, Chapter 35, pp. 395-398.

Ulmsten et al., "An Ambulatory Surgical Procedure Under Local Anesthesia for Treatment of Female Urinary Incontinence," *Int. Urogynecol. J.*, 1996, 7:81-86.

Ulmsten et al., "Different Biomedical Composition of Connective Tissue in Continent and Stress Incontinent Women," *Acta Obstet. Scand.*, 1987, 66:455-457.

Ulmsten, "Female Urinary Incontinence—A Symptom, Not a Urodynamic Disease. Some Theoretical and Practical Aspects on the Diagnosis and Treatment of Female Urinary Incontinence," *Int. Urogynecol. J.*, 1995, 6:2-3.

Ulmsten and Petros, "Intravaginal Slingplasty (IVS): An Ambulatory Surgical Procedure for Treatment of Female Urinary Incontinence," *Scand. J. Urol. Nephrol.*, 1995, 29:75-82.

Ulrstem et al., "A Multicenter Study of Tension-Free Vaginal Tape (TVT) for Surgical Treatment of Stress Urinary Incontinence," *Int. Urogynecol. J.*, 1998, 9:210-213.

Ulmsten et al., "A three-year follow up tension free vaginal tape for surgical treatment of female stress urinary incontinence," *Br. J. Obstet. Gynecol.*, 1999, 106:345-350.

Ulmsten et al., "The unstable female urethra," *Am. J. Obstet. Gynecol.*, 1982, 144:93-97.

Webster and Kreder, "Voiding Dysfunction Following Cystourethropexy: Its Evaluation and Management," *J. Urol.*, 1990, 144:670-673.

Winter, "Peripubic Urethropexy for Urinary Stress Incontinence In Women," *Urology*, 1982, 20(4):408-411.

Woodside and Borden, "Suprapubic Endoscopic Vesical Neck Suspension for the Management of Urinary Incontinence in Myelodysplastic Girls," *J. Urol.*, 1986, 135:97-99.

Zacharin and Hamilton, "Pulsion Enterocele: Long-Term Results of an Abdominoperineal Technique," *Obstet. Gynecol.*, 1980, 55(2):141-148.

Zacharin, "The suspensory mechanism of the female urethra," *J. Anat.*, 1963, 97(3):423-427.

U.S. Appl. No. 60/362,806, filed Mar. 7, 2002.

U.S. Appl. No. 60/380,797, filed May 14, 2002.

U.S. Appl. No. 60/402,007, filed Aug. 8, 2002.

U.S. Appl. No. 60/414,865, filed Sep. 30, 2002.

Complaint for Declaratory Judgment, *American Medical Systems, Inc.* v. *Mentor Corporation* dated Oct. 28, 2003.

Complaint for Patent Infringement, *Mentor Corporation* v. *American Medical Systems, Inc.* dated Feb. 20, 2004.

Answer and Counterclaim of American Medical Systems, Inc. *Mentor Corporation* v. *American Medical Systems, Inc.*, Civ. Case No. 04-1000 DWF/SRN dated Mar. 11, 2004.

Answer and Counterclaim, *American Medical Systems, Inc.* v. *Mentor Corporation*, Civ. No. 03-5759 dated Mar. 15, 2004.

Amended Answer and Counterclaim, *American Medical Systems, Inc.* v. *Mentor Corporation*, Civ. No. 03-5759 dated Mar. 30, 2004.

Plaintiff's Reply to Counterclaim, *Mentor Corporation* v. *American Medical Systems, Inc.*, Civ. No. No. 04-1000 dated Mar. 30, 2004.

AMS's Reply to Mentor's Counterclaim, *American Medical Systems, Inc.* v. *Mentor Corporation*, Civ. No. 03-CV-5759 dated Apr. 5, 2004.

Order dismissing cases Civ. No. 03-5769 and Civ. No. 04-1000 dated Sep. 16, 2004.

Hardiman, et al. Cystoele repair using polypropylene mesh. Br. J. Obstet. Gynaecol. 107: 825-26 (2000).

Jacquetin. Utilisation du "TVT" dans la chirurgie . . . J. Gynecol. Obstet. Biol. Reprod. 29: 242-47 (2000).

deTayrac, et al. Prolapse repair by vaginal route using . . . Int. Urogynecol. J. (published online May 13, 2006).

\* cited by examiner

METHOD AND IMPLANT FOR CURING CYSTOCELE

The present invention concerns the technical field for the treatment of cystocele, in particular in the elderly woman.

In general, cystocele phenomena result from the slackening of the suspension tissue of the urinary and genital organs, provoking disorders that require surgery.

Thus, it has been provided attempts to reconstruct the natural system for the suspension of organs affected by this slackening, implementing non-resorbent sutures or reinforcement strips. However, these techniques are not always satisfactory, in particular due to the requirement for a heavy surgical intervention, inducing a dissection of the anatomic regions not involved by the surgical repair for the non-resorbent sutures.

So as to try to overcome these drawbacks the patent application FR 2 785 521 provides an implant wherein a support body from which two suspension cords at the end of which anchoring elements intended to form sutures on regions considered to be anatomically stable. This implant is then inserted by laparoscopy, thereby reducing the surgical procedure.

However, such an implant has not been able for providing effective suspension, mainly due in particular to the stress applied to the regions considered to be anatomically stable. In addition, this type of implant does not have great stability in space in the conditions of use.

Therefore, the need appeared for an implant providing on one hand, better implant insertion stability and on the other hand, a technique that provides optimum stability while providing a maximum reduction of the patient's trauma.

Thus, in order to achieve these objectives, the invention concerns an implant for the treatment of cystocele, presenting a thin and supple structure and comprising a support body from which two anterior suspension straps extend on both sides of a sagittal plane of the support body and two posterior suspension straps also extend on both sides of the sagittal plane.

According to an essential characteristic of the invention, the implant also comprises so-called middle suspension straps, extending from the support body on both sides of the sagittal plane and between the anterior and posterior straps.

The implementation of six suspension straps then provides better distribution of the effort acting on the support body on the anatomic anchoring points of the straps, while guaranteeing better orientation in space of the support body implanted in the patient.

According to a preferred but not strictly necessary characteristic of the invention, the anterior suspension straps are each intended to be fitted in one of the two ischeo-pubic foramen still called obturators or obturated foramen and, for this purpose, having a length exceeding 100 mm and, preferably, exceeding 120 mm.

According to another characteristic of the invention, the longitudinal axes of the anterior straps form an angle $\alpha$ exceeding 45° and, preferably but not strictly necessarily, an angle $\alpha$ between 100° and 180° and, preferably between 115° and 170°. It should be noted that according to a preferred embodiment of the invention, the sagittal plane forms an axis of symmetry of the implant and thereby bisecting the angle $\alpha$.

According to another characteristic of the invention, the longitudinal axes of the posterior straps form an angle $\beta$ that is not zero. Thereby, the posterior straps are not to be considered to be parallel. Preferably, but not strictly necessarily, the angle $\beta$ exceeds 10° and is preferably between 10° and 75° or even between, 100° and 180° according to the disorder treated.

Preferably, the length of the posterior straps exceeds 100 mm and preferably 120 mm.

According to another characteristic of the invention, the middle suspension straps also exceed 100 mm and, preferably 120 mm.

According to another preferred but not strictly necessary characteristic of the invention, the shape of the support body is substantially rectangular. In a preferred but not strictly necessary characteristic, the support body is between 60 mm and 90 mm long and between 44 mm and 60 mm wide.

According to a preferred embodiment of the invention, the anterior straps substantially extend from the anterior corners of the support body and the posterior straps also extend from the posterior corners of the support body.

The invention also concerns a surgical technique for the insertion of said implant and the treatment of cystocele.

According to the invention, the main characteristic of this technique consists in inserting each one of the anterior suspension straps into one of the ischio-pubic foramen, also known as obturators or obturated foramen.

As for the middle suspension straps they are each placed either in the middle transelevator region, or into an obturated foramen in its infero-posterior region.

The posterior straps are either trans-fixed in the uterosacral ligaments or placed across the uterosacral ligaments then in the transgluteal region, preferably but not exclusively across the sacrosciatic ligaments.

It should be noted that, according to this technique, the hold is mainly provided by friction between the implant and the tissues crossed and, more specifically, by friction between the suspension arm and the muscle tissue crossed.

Preferably, this technique is embodied during so-called mini-invasive surgery, using approach routes in the vicinity of organs to treat, so as to reduce the time of surgery and blood loss. It is thereby possible to obtain a short post-surgical period with minimum patient discomfort. In addition, the simplicity of this technique makes it easy to reproduce and reduces the training required by surgeons.

The invention also concerns an introduction device that may be used without it being absolutely necessary according to the meaning of the invention for the insertion of the implant as disclosed above.

The introduction device according to the invention comprises an introduction member with a supple structure and a shape similar to that of the implant and which comprises:
- a hollow body defining a cavity for the reception of the body of the implant,
- tubular branches extending from the hollow body, each defining a cavity for the reception of an implant suspension strap,
- means of traction extending from the end of each branch of the introduction member,
- and means for cutting at least the hollow body of the introduction member.

According to one characteristic of the invention, the means of traction comprise a semi-rigid needle for each tubular branch.

According to the invention, the means for cutting may be implemented in any appropriate way, such as for example, through a line of lesser resistance likely to break when a traction is carried out at both tubular branches opposite of the introduction member.

According to a preferred but not strictly necessary characteristic of the invention, the means for cutting comprise at least one aperture for the passage of a cutting tool. Preferably, the body of the introduction member comprises a series of apertures located close to a line corresponding to the sagittal plane of the implant as well as between the tubular branches.

According to another characteristic of the invention, the introduction device comprises an implant in accordance with the invention, placed in the cavity of the hollow body and the tubular branches of the introduction member. Preferably but not strictly necessarily, the implant is free inside the introduction member.

To facilitate the surgeon's work, according to another characteristic of the invention, the introduction device also comprises at least an ancillary surgical material that comprises an elongated perforator guide or trocar whose end is intended to be introduced in the body of the patient, the other end of which is fitted with a handle.

According to a characteristic of the invention, the perforator guide is curved in one plane. Preferably, but not strictly necessarily, the curved shape of the perforator extends over an angular sector exceeding 140° and, preferably but not necessarily, inferior to 180° and, preferably, between 150° and 170°. Preferably, the curved portion of the perforator guide is then curved with a radius of between 30 mm and 60 mm and, preferably, for the portion of the perforator guide extending from the handle to the end intended to be introduced in the patient's body of between 40 mm and 50 mm, the outer part of the perforator is then curved with a variable radius.

According to another characteristic of the invention, the perforator guide has a helicoid shape at the opposite end of the handle or distal end. Preferably, the perforator guide then has the shape of a portion of helicoid spire extending over an angle of between 180° and 360° and, preferably, between 255° and 270°. Similarly, the spire of the perforator guide has preferably a radius of curvature between 20 mm and 40 mm, with a pitch between 15 mm and 25 mm.

According to another characteristic of the invention, to reduce the trauma that the patient's body undergoes during the introduction of the implant, the introduction device also comprises a tubular casing whose shape is complementary to that of the perforator guide. This tubular casing is then made to be fit on the perforator guide and to remain in the patient's body after removal of the perforator guide to define a tunnel for the passage of the means of traction of the introduction member. The tubular casing is then removed, after passage of the means of traction when the introduction device is removed.

According to the invention, the tubular casing may be made of any supple biocompatible material such as, for example, but not exclusively, PVC.

Different other characteristics of the invention follow from the above description with reference to the appended drawings that illustrate different embodiments of the implant according to the invention, as well as introduction members making the insertion of the said implant possible.

Moreover, it should be noted that the different characteristics of the invention disclosed above and hereafter, may be combined in different alternatives, with relation to the disorder to treat.

A preferred application of the invention is for the treatment of cystocele. For this purpose, the invention purposes an implant more particularly designed for this disorder and on the whole indicated by reference 1 in FIG. 1. The implant 1 has a thin and supple structure and is made of an adapted bio-compatible material, such as, for example, a synthetic, woven or non woven, or knit material made of polypropylene or polyester fibres. Such a synthetic material may or may not be coated with products favouring cell growth. Similarly, the implant according to the invention, may be made of natural materials such as "fascia latta" or even any biological or synthetic resorbent material.

Figure 1:
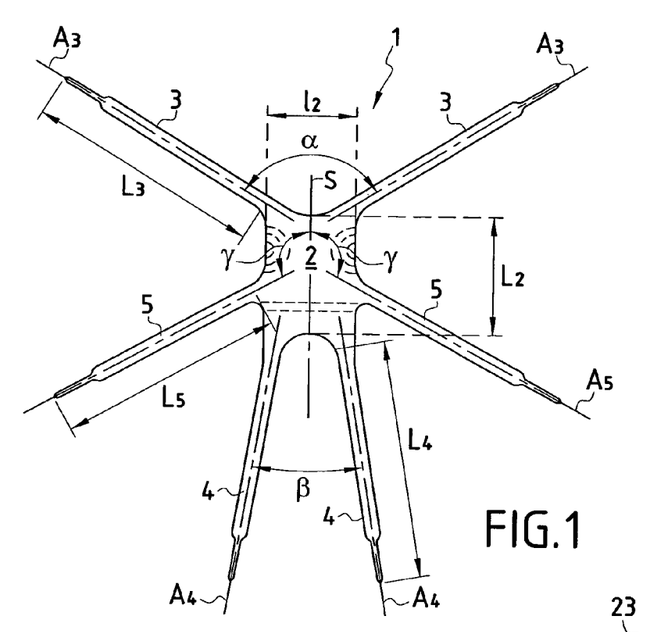
FIG. 1 is an elevation front view of an implant according to the invention, more particularly intended for the treatment of cystocele.

According to an essential characteristic of the invention, implant 1 comprises a support body 2 from which two anterior suspension straps 3 extend on both side of a sagittal plane S. The implant also comprises two posterior suspension straps 4 also extending on each side of the sagittal plane S. Furthermore, implant 1 comprises two middle suspension straps 5 that extend from the support body 2 on sides of sagittal plane S, between the corresponding anterior straps 3 and posterior straps 4.

According to the example shown, the shape of support body 2 is substancially rectangular, without such a shape being considered as necessary according to the invention and the anterior and posterior suspension straps 3 and 4, each extend from a corner of the body 2. It should be noted that, preferably, sagittal plane S corresponds to a plane of symmetry of implant I.

According to a preferred characteristic, related to the technique for the implementation provided by the invention, anterior straps 3 are more particularly intended to be introduced in one of the two ischio-pubic foramen of the subject to treat. For this purpose, the longitudinal axes $A_3$ of anterior straps 3 form an angle $\alpha$, preferably but not necessarily exceeding 45', preferably between 100° and 180°, preferably between 115 and 170°. In addition, to enable easy insertion of anterior straps 3 in the corresponding ischio-pubic or obturated foramen, the length of the anterior straps $L_3$, measured between the distal end of each anterior strap 3 and support body 2, exceeds 100 mm and preferably is equal to or exceeds 120 mm.

As for the posterior straps 4, and as will appear subsequently, posterior straps 4 are more particularly intended to pass through uterosacral ligaments and, for this purpose, the longitudinal axes $A_4$ of posterior suspension straps 4 form an angle $\beta$, preferably but not exclusively not zero, preferably exceeding 10° and, even more preferably, between 10° and 75°. It should be noted that, to facilitate the insertion, the length $L_4$ of posterior suspension straps 4, measured between the distal end of the straps and support body 2, preferably exceeds 100 mm, even more preferably equals or exceeds 120 mm.

As for the middle suspension straps 5, they are intended to be passed across the uterosacral ligaments, and for this purpose, the longitudinal axis $A_5$ of each middle suspension strap 5, forms, along with the anterior part of sagittal plane, an angle $\gamma$, preferably but not necessarily of between 100° and 140° and, preferably between 110° and 130° and, in even more preferably, of between 115° and 125°. Such as the other anterior and posterior suspension straps 3 and 4, the length $L_5$ of middle suspension straps 5, measured between the distal end of the middle suspension straps 5 and support body 2, preferably exceeds 100 mm and, more particularly preferably, exceeds or equals 120 mm.

Moreover, the width of suspension straps 3, 4, 5 is chosen, preferably but not exclusively, to be between 5 mm and 15 mm and, for example, about ten millimeters.

Implant 1, as described above, is intended to be inserted in the anterior vaginal wall of a patient. For this purpose, for reducing the dissection of this region and the resulting trauma to a minimum, the invention proposes that the surgeon use one or several elongated perforator guides 10, such as those more particularly shown on FIGS. 2 and 3 to 5.

Such a perforator guide 10 commonly comprises an elongated body or chuck 11, one end 12 of which is intended to be introduced in the body of the subject to be treated and the other end 13 is fitted with a handle 14. It should be noticed that introduction end 12 is preferably formed by a foam tip, that is, a non-traumatic tip that is not likely to would or cut the tissue in which it has to be introduced.

Figure 2:
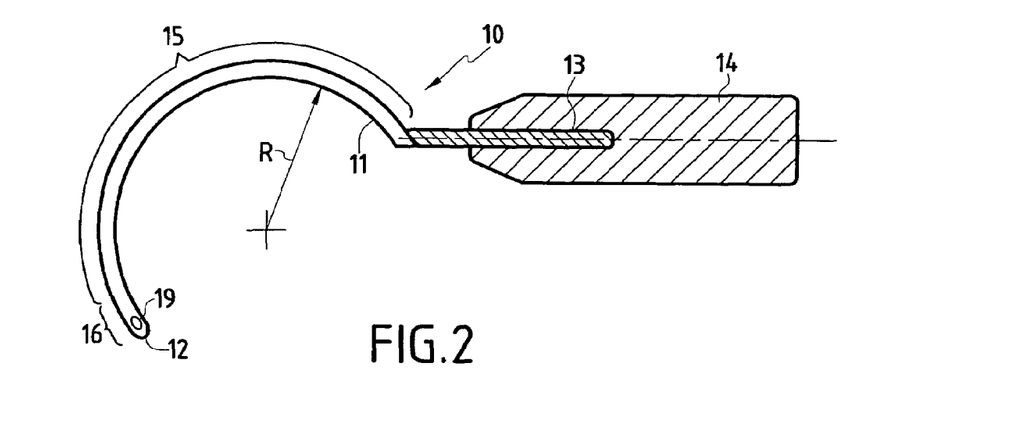
FIG. 2 is an elevation view, partially removed, of a perforator guide that may be used for the insertion of an implant according to the invention with a curved shape.

According to one embodiment shown in FIG. 2, perforator guide 10 is curved in one plane. This curved shape in one plane is especially adapted for the insertion of suspension straps in the anterior and posterior regions of the obturated foramen. Preferably but not strictly necessarily, the curved portion of the perforator guide has a radius of curvature R of between 30 mm and 60 mm and, preferably, for portion 15 of perforator guide 10 extending from handle 14 to end 12, between 40 mm and 50 mm, the outer part 16 of the perforator guide 10 thereby has a variable radius of curvature.

Figure 3:
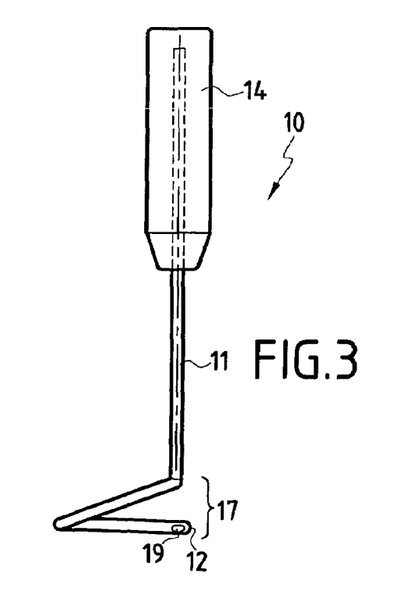
FIG. 3 is an elevation view of another embodiment of a perforator guide according to the invention, with a helicoid-shaped introduction end.
Figure 4:
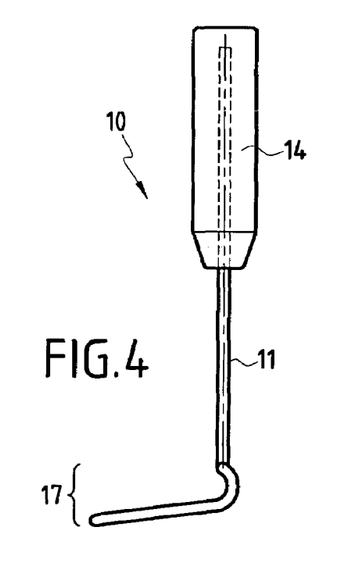
FIG. 4 is a left view of the perforator guide according to FIG. 3.
Figure 5:
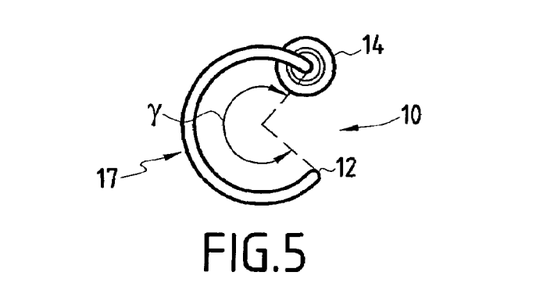
FIG. 5 is a view from below of the perforator illustrated in FIG. 3.

According to another implementation of perforator guide 10, shown on FIGS. 3 to 5, the elongated body 11 of guide 10 has a helicoid shaped end 17, also adapted for the insertion of suspension straps in the anterior or posterior regions of the obturated foramen. Preferably, the distal end 17 of the perforator guide thereby has the shape of a portion of helicoid spire extending over an angle γ of between 180° and 360° and, preferably, between 255° and 270°. Also preferably, spire 17 of the perforator guide has a radius of curvature of between 20 mm and 40 mm, with a pitch of between 15 mm and 25 mm.

The surgical treatment of cystocele, by means of an implant 1 and perforator guides 10, as previously described, is carried out as follows.

The patient to be treated is first given an anaesthetic that may be general, regional or even local, according to the preference of the surgeon and the state of health of the patient. The operating position of the patient on the operating table will be that of usual vaginal surgery, that is with the patient's buttocks slightly outside of the surgical table and the thighs slightly bent on the abdomen.

A dissection of the region of intervention is then carried out by respecting the attachments of the b ladder neck. Traction is first exerted on the neck of the uterus, for example by means of Muze forceps, in order to expose the anterior fornix of the vagina. A vaginal incision, called horizontal pre-cervical incision, may thereby be carried out on the anterior side of the neck of the uterus, cross-wise on the cervical side of the fornix of the vagina, well exposed by the traction. The entire edge of the anterior vaginal section is then taken hold: vaginal skin and Halban's fascia, by means of, for example, three Alis forceps that are drawn upwards to expose the vesico-vaginal plane. A vesico-vaginal detachment is then progressively carried out by everting the anterior vaginal wall. This detachment is halted at the bottom and in the middle, just above the bladder neck, while it is carried out below and laterally up to the arcatus tendinus fascia pelvis. This area of the arcatus tendinus fascia pelvis is then opened toward the obturator foramen, so as to enable the introduction of a finger behind the obturator muscle. Similarly, the detachment practiced at the top, at the level of the vaginal incision, should enable the introduction of a finger against the levator muscle.

Once the dissection is carried out, the first anterior suspension strap 3 may be inserted in the corresponding ischio-pubic foramen. For this purpose, a curved or helicoid perforator guide 10 is used, as previously described, depending on the surgeon's choice. First, a punctiform incision is carried out preferably about 15 mm outside of the ischio-pubic branch at the horizontal level with respect to the clitoris cap. A finger is then inserted behind the obturator foramen, so as to receive the introduction end or tip 12 of perforator guide 10, introduced by the puctiform incision. Perforator guide 10 is then inserted, led by the finger until the anterior vaginal incision.

At this stage, anterior suspension strap 3 is secured on the perforator guide, for example at the level of an eye 19 at the introduction end 12 of this guide. Once secured, the perforator guide is removed, thereby providing a traction on the anterior suspension strap that is then introduced through the obturator foramen.

The same surgical procedure is repeated for the introduction of the second anterior suspension strap 3.

It should be noted that the anterior suspension straps 3 are preferably positioned without traction to prevent the dysuric effect of implant 1 that is placed just above and behind the bladder neck.

The first middle suspension strap 5 is then put in place.

For this purpose, a punctiform incision is made in the genitocrural groove, horizontally with respect to the posterior commissure of the labia majora. Perforator guide 10 is then introduced by this incision to be led through the levator muscle. It should be noted that the end of the perforator guide 10 is then located just within the ischio-pubic branch, one finger placed against the upper side of the levator muscle receiving the tip of the perforator guide to lead it into the anterior vaginal incision.

The end of the middle suspension strap 5 to be placed is then secured at the end 12 of perforator guide 10 which is then removed in the opposite direction to bring along with the middle suspension strap 5.

The same surgical procedure is then repeated for the insertion of the second middle suspension strap 5.

It should be noted that the middle suspension straps 5 are preferably placed, without any traction or mechanical bias, to prevent the cord effect of the fibroid prosthetic strap in the latero-vesicovaginal grooves.

According to an alternative implant, the middle suspension straps 5 may also be implanted through a corresponding obturated foramen, in its lower posterior part opposite to the ischium.

At this stage of the insertion of implant 1, the anterior edge of the implant is preferably secured by one or several, preferably two or three resorbent stitches at the anterior side of the neck of the uterus.

The insertion of implant 1 continues by the entry of posterior suspension straps 4. It should be noticed that the posterior suspension straps 4 are essential in case of hysterectomy without conservation of the neck.

A first posterior suspension strap 4 is placed through the base of the broad ligament and through the base of the uterosacral ligament. For this purpose, perforator guide 10 is introduced from the rear vaginal wall to the front through the uterosacral ligament. Posterior strap 4 is then secured to the perforator guide and drawn in a reverse direction from front to back through the uterosacral ligament.

The same surgical procedure is repeated for the insertion of the second posterior suspension strap 4.

The posterior suspension straps 4 may then be left free after crossing the uterosacral ligaments or on the contrary each be secured by a resorbent suture to the prerectal plate.

According to an alternative of the invention, the posterior suspension straps 4 are each passed first through the corresponding uterosacral ligament, then through the sacrosciatic ligament by means of the perforator guide 10 that will have gone into the transgluteal pathway zone.

The operation finishes with the closing of the vaginal incision by means of resorbent continuous suture as well as the closing of the punctiform incisions also by means of resorbent thread.

At the end of the intervention, a vaginal wick is inserted as well as a bladder probe that are removed forty-eight hours after the intervention. The post-urinary residues are then measured by probe, to make sure that the bladder emptying is satisfactory, so as to authorise the patient's discharge.

The intervention to treat the cystocele lasts about one hour and the average period of hospitalisation is four days. The patient's activity will be restricted for one month and a bath should be avoided during the same period of time. Finally, it is advisable to plan for six weeks of sexual abstinence after the operation.

Therefore, the technique proposed only treats the disorder, that is the imbalance in the pelvic statics and thereby restores as normal an anatomy as possible by preserving the individual's body image. This technique advantageously keeps the healthy organs or does not have an unfavourable effect on the pelvic statics. Indeed, the possibility of cancer will have been eliminated by the pre-surgical assessment and it will be possible to provide reliable gynaecological monitoring after the surgery.

Moreover, there are very low risks of pelvic genital cancer and, in addition, the treatment proposed by the invention does not complicate subsequent access to the genital organs.

As indicated above, the implant according to the invention is preferably inserted so as not to have any residual tension after insertion. To facilitate this surgical procedure, an alternative of the intervention proposes the use of an introduction member, more particularly shown on FIG. 6 and indicated as a whole in reference 20.

This introduction member has a supple structure and its shape is similar to that of the implant. Introduction member 20 is preferably made of a bio-compatible polymer from the family of plastics with a low friction coefficient, such as, for example, polyethylene. Introduction member 20 thereby comprises a hollow body 21 defining a cavity for the reception of body 2 of implant 1. Introduction member 20 also comprises tubular branches 22 that extend from the hollow body 21 and that each define a cavity for the reception of a suspension strap 3, 4 and 5 of the implant 1. Each tubular branch 22 thereby has means of traction 23 extending from the corresponding free end of branch 22. The means of traction 23 may be provided in any appropriate manner such as, for example, systems for the coupling of the ends of branches 22 on a perforator guide 10. According to the example illustrated in FIG. 6, the means of traction 23, comprise for each branch 22, a soft or semi-rigid needle with a non-traumatic or foam tip. Such a needle may be made of the same material as the material used for the introduction device 20 or, more generally, of a biocompatible plastic, preferably with a low friction coefficient.

Finally, introduction member 20 comprises means for cutting 24 whose function will appear hereafter, of at least the hollow body 21 of the introduction member 20. The means for cutting 24 may then be carried out in any appropriate manner and, according to the example illustrated, include a series of six apertures 24 made at the periphery of hollow body 21, between each of the tubular branches 22, to enable the passage of a cutting tool to provide the cutting of the hollow body 21 according to lines 25 delimited by the mixed dashes in FIG. 6.

Figure 6:
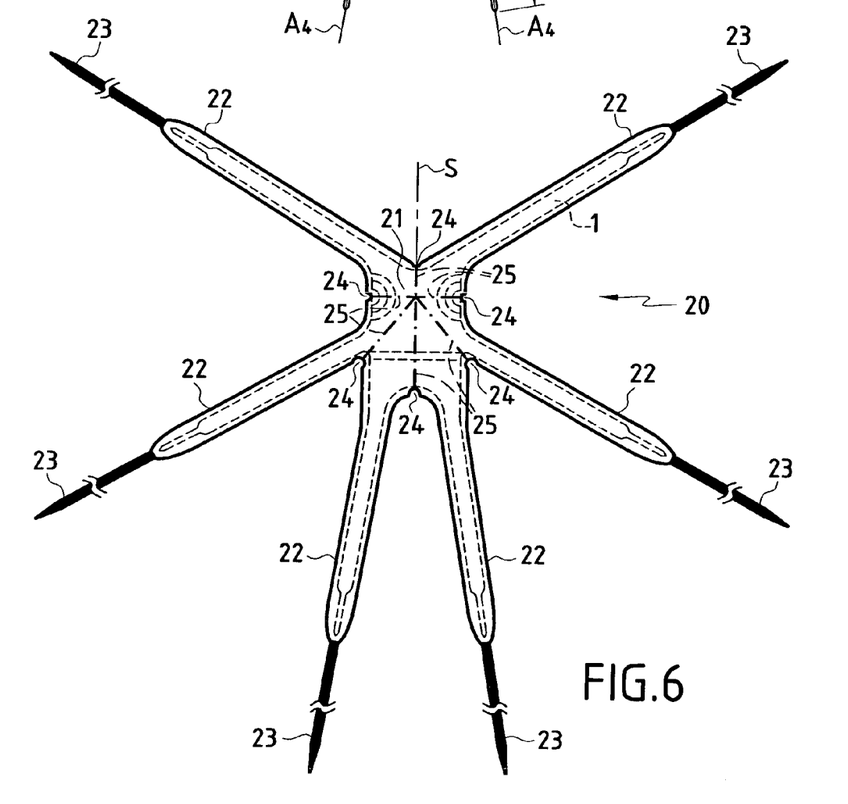
FIG. 6 is a view of an introduction member according to the invention, enabling the insertion of the implant shown in FIG. 1.
Figure 7:
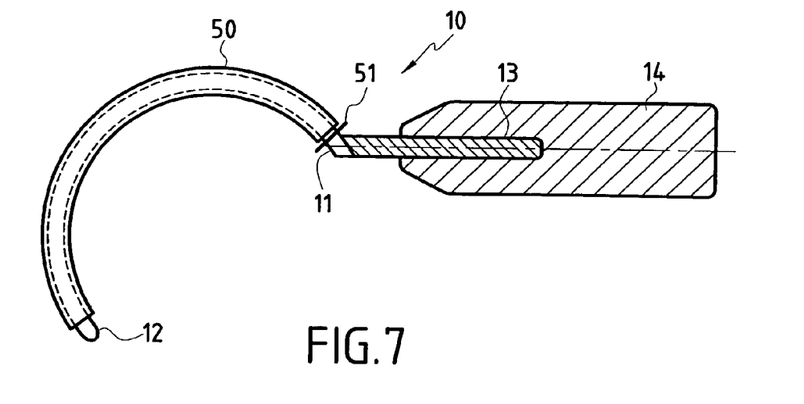
FIGS. 7 to 10 are views, similar to FIGS. 2 to 3, showing alternatives of the perforator guides for the insertion of an implant according to the invention.
Figure 8:
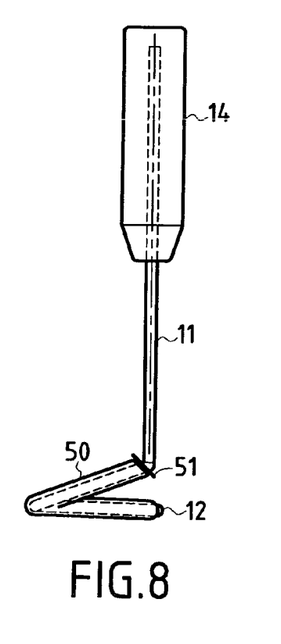
Figure 9:
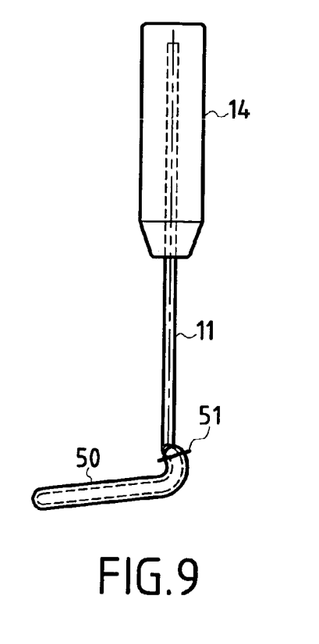
Figure 10:
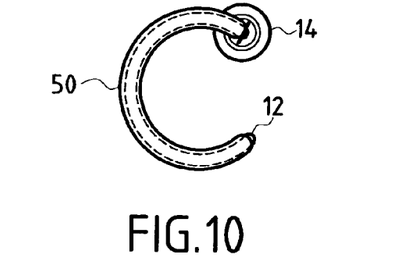

Implant 1 is placed inside of hollow body 21 and tubular branches 22, being preferably free inside of the hollow body and of the tubular branches, so that the stress exerted on introduction member 20 is not transmitted to implant 1 itself.

The insertion of implant 1 by means of introduction member 20 thereby formed, is carried out according to the same surgical procedure described above, the removal and cutting of the introduction member 20 occur after the insertion of the whole suspension branches in the patient's body or, more specifically, corresponding tubular branches 22. The removal of the different members of the introduction member 20 by the traction exerted two by two on the opposite tubular branches 22 thereby enables the insertion of implant 1, without any stress, on the introduction member, so that it is found in a state that may be qualified as slack.

In the examples of the treatment and operation described above, the introduction device used comprises simple perforator guides 10. Nevertheless, to try to reduce the trauma by abrasion of the tissue areas crossed to a maximum, it is possible to use an ancillary associating the perforator guide 10 to a soft casing 50 whose shape is complementary to that of guide 10, as illustrated in FIGS. 7 and 8 to 10. Casing 50 is inserted on perforator guide 10 that then has a stop device or guard 51 on which casing 50 comes up against during the introduction of perforator guide 10 in the patient's body. Casing 50 is left in the patient's body after removal of perforator guide 10 and before insertion of implant 1, 29, 39. The casing used thereby enables the creation of a channel for the passage of a traction element 23 of the introduction member 20 and wherein a tubular branch 23 and associated suspension strap 3, 4, 5 or a suspension strap 3, 4, 5 may be moved by sliding, so as to adjust the position of implant 1, 29, 39 without abrasion of the tissue crossed. A casing 50 is then used for the insertion of each suspension strap 3, 4, 5. The casings 50 are then removed along with the tubular branches 23 covering the suspension branches of the implant or when the implant is inserted bare after adjusting the implant position.

Thereby, the use of the casings 50 avoids acute inflammatory phenomena and reduces tissue trauma as long as the implant sites consist of very specialised muscle tissue that lost a large part of their ability to quickly regenerate and heal.

Of course, different other modifications may be provided for the invention within the scope of the invention.

The invention claimed is:

1. A system being configured to treat cystocele, comprising an implant having a thin and supple structure and a device for the introduction of an implant, where the implant comprises a support body made of bio-compatible material, from which extend at least:
   two anterior suspension straps on both sides of a sagittal plane,
   two posterior suspension straps on both sides of a sagittal plane,
   and two middle suspension straps on both sides of a sagittal plane and between the anterior and the posterior straps;
   and wherein the device for the introduction of an implant comprises an introduction member that has:
   a supple structure and whose shape is similar to that of the implant;
   a hollow body defining a cavity for the reception of the body of the implant;

tubular branches extending from the hollow body each defining a cavity for the reception of a suspension strap of the implant;

means for traction extending from the end of each of the branches of the introduction member; and means for cutting apertures in at least the hollow body of the introduction member.

2. An implant according to claim 1, wherein a longitudinal axis of the two anterior straps form an angle exceeding 45°.

3. An implant according to claim 2, wherein the angle is between 100° and 180°.

4. An implant according to claim 2, wherein the angle is between 115° and 170°.

5. An implant according to claim 1, wherein a longitudinal axis of the two posterior straps form an angle that is not zero.

6. An implant according to claim 5, wherein the angle exceeds 10°.

7. An implant according to claim 6, wherein the angle is between 10° and 75°.

8. An implant according to claim 6, wherein the angle is between 100° and 180°.

9. An implant according to claim 1, wherein a longitudinal axis of each middle suspension strap and an anterior part of the sagittal plane, forms an angle between 100° and 140°, preferably between 110° and 130°.

10. An implant according to claim 1, wherein a length of each anterior strap exceeds 100 mm.

11. An implant according to claim 1, wherein a length of posterior strap exceeds 100 mm.

12. An implant according to claim 1, wherein a length of each middle strap exceeds 100 mm.

13. An implant according to claim 1, wherein the whole shape of the support body is substantially rectangular.

14. An implant according to claim 13, wherein a length of the support body is between 60 mm and 90 mm and a width of the support body is between 40 mm and 60 mm.

15. An implant according to claim 13, wherein each anterior strap substantially extends from an anterior corner of the support body.

16. An implant according to claim 1, wherein each posterior strap substantially extends from a posterior corner of the support body.

17. An introduction device according to claim 1, wherein the means of traction include a semi-rigid needle for each tubular branch.

18. An introduction device according to claim 1, wherein the means for cutting apertures comprise at least one aperture for the passage of a cutting instrument.

19. An introduction device further comprising an implant according to claim 1 placed in the cavity of the hollow body and the tubular branches.

20. An introduction device according to claim 19, wherein the implant is free inside the introduction device.

21. An introduction device according to claim 1, further comprising an elongated perforator guide or trocar, one end of which is made to be introduced in the patient's body and the other end is equipped with a handle.

22. An introduction device according to claim 21, wherein the shape of the perforator guide is curved in one plane.

23. An introduction device according to claim 22, wherein the curved part of the perforator extends over an angular sector exceeding 140°.

24. An introduction device according to claim 22, wherein the curved part of the perforator guide has a radius of curvature between 30 mm and 60 mm.

25. An introduction device according to claim 21, wherein the perforator guide has a helicoid shape at the end opposite to the handle or a distal end.

26. An introduction device according to claim 25, wherein the distal end of the perforator guide has the shape of a portion of helicoid spire extending over an angle of between 180° and 350°.

27. An introduction device according to claim 26, wherein the spire of the perforator guide has a radius of curvature between 20 mm and 40 mm, with a pitch between 15 mm and 25 mm.

28. An introduction device according to claim 21, further comprising a removable tubular casing whose shape is complementary to that of the perforator guide, intended to be fit on the perforator guide and remain in the patient's body after the removal of the perforator guide to define a tunnel for the passage of the means of traction of the introduction member.

29. A procedure for the treatment of cystocele in women, comprising:
    using an implant and a device for the introduction of an implant according to claim 1;
    inserting the implant in the body of the patient by placing:
        each of the anterior suspension straps in an obturated foramen,
        each of the middle suspension straps in a corresponding middle translevator region,
        each of the posterior suspension straps in a corresponding uterosacral region,
        and the support body in an anterior vaginal wall.

30. A procedure for the treatment of cystocele in women, comprising:
    using an implant and a device for the introduction of an implant according to claim 1;
    inserting the implant in the body of the patient by placing:
        each of the anterior suspension straps in an obturated foramen,
        each of the middle suspension straps in an inferoposterior region of the corresponding obturated foramen,
        each of the posterior suspension straps in a corresponding uterosacral region,
        and the support body in an anterior vaginal wall.

31. A procedure for the treatment of cystocele in women according to claim 29, further comprising placing each of the posterior suspension straps through the corresponding uterosacral region.

32. A procedure for the treatment of cystocele in women according to claim 29, further comprising placing each of the posterior suspension straps through the corresponding uterosacral region and in the corresponding transgluteal region.

33. A procedure for the treatment of cystocele in women according to claim 32, further comprising placing each of the posterior suspension straps through the corresponding uterosacral region and through the corresponding sacrosciatic ligament.

34. An implant and a device for the introduction of an implant according to claim 1, wherein said bio-compatible material is selected from the group consisting of: a synthetic material; a woven material; a non-woven material; a knit material; polypropylene fibres; polyester fibres; a material coated with products favouring cell growth; a natural material; fascia latta; a biological resorbent material; and a synthetic resorbent material.

* * * * *